United States Patent
Birkett et al.

(10) Patent No.: US 7,110,890 B2
(45) Date of Patent: Sep. 19, 2006

(54) AUTO-ANALYSIS FRAMEWORK FOR SEQUENCE EVALUATION

(75) Inventors: Thomas E. Birkett, Stockton, CA (US); Puneet Suri, Redwood City, CA (US); Kai C. Yung, Livermore, CA (US); Sylvia H. Fang, Fremont, CA (US); Salil Kumar, Sugar Land, TX (US); Benjamin B. Jones, San Ramon, CA (US); Jon M. Sorenson, Oakland, CA (US); Yuandan Lou, Cupertino, CA (US); Catherine E. Frantz, Los Altos Hills, CA (US)

(73) Assignee: Applera Corporation, Foster City, CA (US)

( * ) Notice: Subject to any disclaimer, the term of this patent is extended or adjusted under 35 U.S.C. 154(b) by 90 days.

(21) Appl. No.: 10/650,470

(22) Filed: Aug. 28, 2003

(65) Prior Publication Data
US 2004/0121369 A1  Jun. 24, 2004

Related U.S. Application Data

(60) Provisional application No. 60/407,439, filed on Aug. 28, 2002.

(51) Int. Cl.
*G06F 7/38* (2006.01)
(52) U.S. Cl. .......................... 702/31; 702/32; 702/182; 702/183
(58) Field of Classification Search ................ 702/19, 702/31, 32, 119–123, 182, 183; 340/359.13; 600/509; 435/286.3
See application file for complete search history.

(56) References Cited

U.S. PATENT DOCUMENTS

| 6,103,518 A | * | 8/2000 | Leighton | 435/286.3 |
| 6,909,974 B1 | * | 6/2005 | Yung et al. | 702/31 |
| 6,917,829 B1 | * | 7/2005 | Kwong | 600/509 |

FOREIGN PATENT DOCUMENTS

| WO | WO 01/09618 A1 | 2/2001 |
| WO | WO 01/79949 A2 | 10/2001 |

OTHER PUBLICATIONS

Siepel et al., "An Integration Platform For Heterogeneous Bioinformatics Software Components", IBM Systems Journal, vol. 40, No. 2, 2001, pp. 570-591.
Sutherland et al., "Computer Network For Data Acquisition, Storage and Analysis", Journal of Photochemistry and Photobiology B: Biology, vol. 40, No. 1, 1997, pp. 14-22.
International Search Report, PCT/US03/26804, Date of mailing Apr. 6, 2005.

* cited by examiner

*Primary Examiner*—Marc S. Hoff
*Assistant Examiner*—Felix Suarez (57) ABSTRACT

An automated system for evaluating biological samples which includes a centralized registry that contains protocols and configuration information for both instruments and analysis applications. The registry provides for improved automation of biological process runs using an autoanalysis applications manager component or daemon, which accesses and transmits the appropriate protocol and configuration information to selected instruments and/or applications. This information is used to instruct data capture by the biological instruments and direct the analysis of the data by the analysis applications.

31 Claims, 10 Drawing Sheets

FIG. 6D

AUTO-ANALYSIS FRAMEWORK FOR SEQUENCE EVALUATION

CLAIM OF PRIORITY

This U.S. patent application claims priority to U.S. Provisional Patent Application No. 60/407,439, entitled "Auto-Analysis Framework for Sequence Evaluation", filed Aug. 28, 2002 which is hereby incorporated by reference.

BACKGROUND

1. Field

The present teachings relate to biological laboratory instruments and, more particularly to a system and methods for integrating large numbers of instruments and analysis applications into an automated framework.

2. Description of the Related Art

Biological analysis is often a complex process that involves many different instruments and associated analysis applications. In genomic and molecular biological studies, large numbers of samples may be processed by sequencers, fluorometers, mass spectrometers, and other instruments to provide data, indicative of the composition or expression of nucleotide or protein components comprising the sample. Captured data is subsequently provided to one of a number of different applications for further processing and analysis. The analysis applications are typically software-based and may perform such tasks as sequence determination, mutational analysis, single nucleotide polymorphism (SNP) identification, etc. In certain implementations, a number of applications may be required to process the data from a variety of different samples in order to complete the analysis. These applications may be configured to operate serially wherein the resultant data output by one application is used as input for another application. When operating in this mode, the data must be properly organized and configured in the manner which is expected by each application. Typically, such operations are performed by an investigator and means to better automate the process are lacking in the industry. Likewise, parallel data processing to achieve improved throughput often requires investigator coordination, monitoring, and review thus limiting the potential to more fully automate the analysis process.

As biological laboratories become increasingly complex with more associated instruments and analysis applications, the difficulty of integrating the analysis applications and instruments into a unified system amenable to automated analysis becomes more complex. Hence, there is a need for systems and methods which permit improved integration of instruments and analysis applications in biological laboratory environment.

SUMMARY

The aforementioned needs are satisfied by the present teachings which, in one aspect, comprise a system for integrating a plurality of biological data acquisition instruments that obtain electronic data from physical data samples with a plurality of data analysis applications. The system comprises a plurality of instrument components associated with the instruments that capture identification information and data from the biological samples and at least one registry component defining a suitable instrument protocol for each of the plurality of instrument components and an application protocol for each of the data analysis applications. In various embodiments, the system further comprises an application manager component that communicates with the plurality of instrument components and the plurality of data analysis applications and further has access to the information contained in the at least one registry component. The application manager utilizes the information contained in the at least one registry component to determine appropriate data and information to be sent and received from the biological instruments, as well as, determining the type and format of data to be provided to the analysis applications. In one aspect, the applications manager component further recognizes an analysis protocol to be used to perform a desired data analysis procedure. The applications manager sends/receives data, information and instructions to/from analysis applications so as to provide a means to conduct multi-step analysis which require interaction between a plurality of software applications and/or instruments.

The applications manager may further provide a user interface whereby an investigator can program or schedule biological analysis routines for one or more samples by selecting instruments identified in the registry to capture the data from the biological sample and selecting the one or more analysis applications from the registry to receive and process the electronic data. In various embodiments, additional instruments and analysis applications can be incorporated into the system by registering the instrument component protocols and analysis application protocols in the registry as desired or as they become available.

In another aspect, the present teachings provide a system for integrating a plurality of biological data instruments that acquire electronic data from physical biological samples with a plurality of discrete data analysis applications that receive the electronic data from the biological data instruments. The system may be configured to operate in such a manner so as to provide a degree of transparency between the instruments and applications such that the data formatting, transmission, and storage is handled without special or custom configuration of either the instruments or applications. This feature improves scalability of the system and allows for a more flexible means to maintain/upgrade components of the system.

The system further comprises a plurality of instrument components respectively associated with the biological data instruments and the at least one registry containing instrument protocols for each of the plurality of instruments and protocols for each of the data analysis applications, wherein the data analysis protocol includes a messaging protocol. In this aspect, the system further comprises an application manager that communicates with the plurality of instrument components and the plurality of data analysis applications via a standardized communications protocol wherein the application manager has access to the at least one registry and includes an associated user interface such that the user can program a series of biological analysis operations to be performed via the user interface such that selected biological samples may be processed by desired instruments. Upon completion of the processing of the biological samples, the data may be made available to selected data analysis applications for subsequent processing. In this aspect, the application manager automatically makes the data available to the data analysis application(s) via an appropriate communications protocol by notifying the data analysis application(s) of the location and/or address of the data or by distributing the information directly to the application itself.

In yet another aspect, the present teachings describe a system for integrating a plurality of biological data instruments that obtain data from samples, with a plurality of data analysis applications, wherein the system comprises a plurality of instrument components respectively associated with the instruments that capture identification information from the samples, at least one registry containing instrument protocols for each of the plurality of instrument components and protocols for each of analysis applications wherein the protocols for the analysis applications includes a format protocol indicative of the format required by a selected analysis application to process data from one of the plurality of instruments. The system in this aspect further comprises a management component that communicates with a plurality of instrument components and the plurality of analysis applications and has access to the at least one registry. In this particular implementation, the manager component includes a user interface that provides a means for a user to select one or more instruments to be used to conduct a biological analysis. The user interface further provides means for selecting particular samples to be analyzed and can further direct the resultant data obtained from particular instruments to be provided to appropriate analysis applications. In this aspect, the applications manager provides instructions to the instrument component associated with selected instruments such that the instrument component will output the data in a desired format as indicated by the format protocol in the registry and specified for the selected analysis application that is to receive the data from the instrument component.

From the foregoing, it will be appreciated that the system and methods of the present teachings permit a scalable environment in which to conduct biological analysis and further provide greater flexibility in terms of adding or changing instruments and analysis applications. Furthermore, integration of the application manager into the system improves data transparency throughout the analysis environment and facilitates design and implementation of automated routines. These and other objects and advantages of the present teachings will become more apparent from the following description taken in conjunction with the accompanying drawings.

DETAILED DESCRIPTION OF CERTAIN EMBODIMENTS

Figure 1:
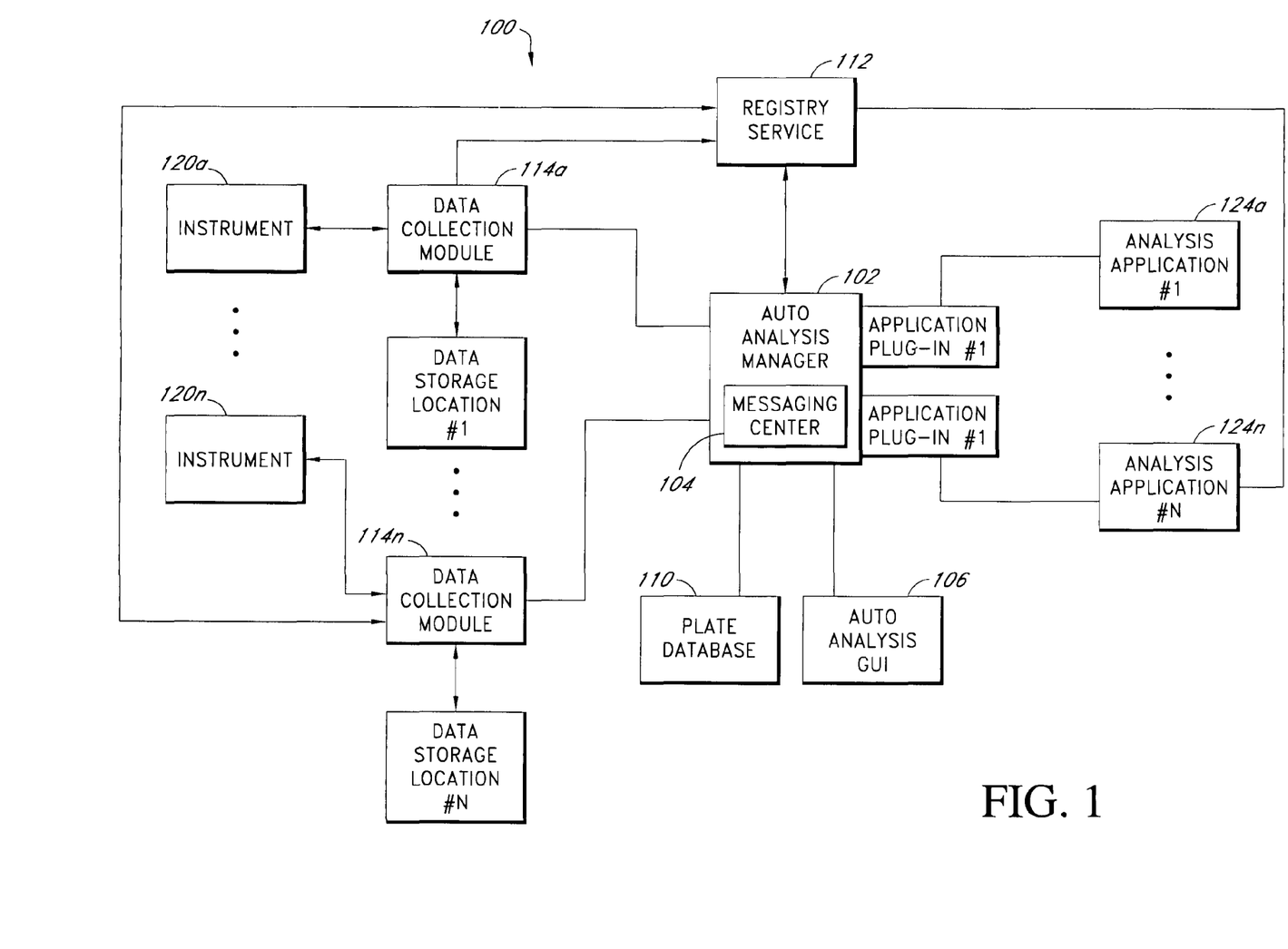
FIG. 1 is a block diagram of a biological analysis system with a management and registry component that permit enhanced automation of the system.

Reference will now be made to the drawings wherein like numerals refer to like parts throughout. FIG. 1 is a block diagram that graphically illustrates a biological analysis system 100. As is shown in FIG. 1, the biological system 100 includes a plurality of instruments 120a–120n used to evaluate physical biological samples and provide electronic signals/data indicative of the constituent components or information obtained from the biological samples tested. The instruments 120a–120n may include known devices, such as sequencers, fluorometers, mass spectrometers, bioinformatics assay devices, spectrometers, and the like. As is also shown in FIG. 1, the biological analysis system further includes a plurality of analysis applications 124a–124n. The analysis applications are designed to receive the information generated by the instruments 120a–120n and further process this data. The analysis applications may, for example, include software programs that contain algorithms and processes that determine sample sequences or evaluate expression data from the information provided by the instrument and may also perform a multiplicity of other analyses, such as mutational analysis of the sample data, single nucleotide polymorphism (SNP) identification, base calling and the like. The instruments 120a–120n and the analysis applications 124a–124n may comprise any of a number of different instruments and analysis applications known in the art.

In existing biological analysis systems, the incorporation of new applications or instruments into the analysis environment often requires significant efforts to modify the existing architecture in order to support the new instrumentation and/or applications. For example, if a new application is to be desirably integrated into the environment, those instruments that will provide data to the new application may have to be reprogrammed/reconfigured. In one aspect, reconfiguration in this manner is necessary to insure that the data generated by the instruments is provided to the analysis application in the proper format and at the proper time. Alternatively, human intervention may be required to reformat data generated by particular instruments into an appropriate format for a selected analysis application. Both of these considerations increase the cost and difficulties of operating a large, complex biological analysis system.

In general, existing biological analysis environments are not well suited to accommodate changes in the individual components (e.g., instruments and applications) and, furthermore, maintaining a highly automated environment necessarily imparts a large degree of rigidity into many aspects of conventional systems including protocols, data formats, run scheduling, allocation of application resources and the like.

In contrast, as illustrated in FIG. 1, the biological analysis system 100 includes an autoanalysis manager 102 with an associated message service 104. The autoanalysis manager 102 comprises a daemon or coordination component that communicates with the analysis applications 124a–124n as well as the data collection modules 114a–114n associated with the instruments 120a–120n. As will be discussed in greater detail below, the autoanalysis manager 102 facilitates the transfer of the electronic data from the instruments 120a–120n to the analysis applications 124a–124n in a manner that reduces the need for human intervention. Moreover, the autoanalysis manager also allows for the addition of new instruments 120a–120n or new analysis applications 124a–124n into the biological analysis system 100 without significant reprogramming of the operating systems of either the instruments 120a–120n or the analysis applications 124a–124n. Furthermore, the autoanalysis manager 102 provides a means to efficiently design, schedule, and execute experimental runs and subsequent analyses even in complex environments.

As is illustrated in FIG. 1, the autoanalysis manager 102 is configured to communicate with a registry service 112. The registry service 112 includes identifiers and protocols for each analysis application 124a–124n. Similarly, the registry 112 also includes identifiers and protocol information for each of the instruments 120a–120n. As will also be described in greater detail below, when new instruments or applications are added to the biological analysis system 100, the registry may be updated to include the appropriate identification information and protocols for the newly added component(s). The autoanalysis manager 102 may further use the information in the registry to determine the appropriate format of data and communicate information generated by the instruments 120a–120n to the analysis applications 124a–124n. In one particular implementation, the registry comprises a JAVA naming and directory interface (JNDI) configured for the tasks and functionalities indicated.

As is also illustrated in FIG. 1, the autoanalysis manager 102 has an associated messaging service 104 which broadcasts messages to the instruments 120a–120n and analysis applications 124a–124n. For example, the autoanalysis manager 102 communicates with the data collection modules 114a–114n that are associated with each of the instruments 120a–120n. In various embodiments, the data collection modules 114a–114n represent software or hardware front ends to the instruments 120a–120n and provide signals and information to the autoanalysis manager 102 indicative of the status of sample procedures/processes being performed by the instruments 120a–120n. The aforementioned information may further indicate the data storage locations 116a–116n where the data captured/generated by the instruments 120a–120n can be located. In one aspect, upon receiving status information about a particular sample process from one or more of the data collection modules 114a–114n, the autoanalysis manager 102 induces a messaging service 104 to broadcast a message that one or more of the analysis applications 124a–124n and the autoanalysis manager 102 can be configured to receive. In one particular implementation, the messaging service comprises a JAVA messaging language service (JML) which broadcasts these messages.

As is illustrated in FIG. 1, the autoanalysis manager 102 may also have an associated user interface 106 which allows an individual to interact with the autoanalysis manager 102 to design, configure and schedule an automated analysis run. As will be described in greater detail below, the autoanalysis manager user interface 106 provides an environment which displays available instruments, protocols, and analysis applications which may be configured to perform automated analysis of desired biological samples. The analysis manager further directs the execution of a defined run by instructing the instruments to acquire the appropriate data which may then provided to selected analysis applications 124a–124n in an automated fashion. As is shown in FIG. 1, the autoanalysis manager 102 may also have access to a plate database 110 wherein the plate database 110 includes identification information about sample trays containing a plurality of different physical biological samples. An investigator, through the user interface 106, can access the plate database 110 and then direct particular samples on individual plates to be acquired/evaluated by selected instruments 102. Furthermore, the investigator can define how the corresponding data will be provided to analysis applications 124a–124n for subsequent processing and the type(s) of analyses to be performed.

As is also illustrated in FIG. 1, associated with each analysis application 124 is an application plug-in 126a. The application plug-in 126a comprises a driver configured to operate with the autoanalysis manager 102 which provides a set of definitions/instructions to the autoanalysis manager 102 to thereby allow the autoanalysis manager 102 to communicate with the analysis applications 124a–124n. The use of the plug-in in this instance allows for additional analysis applications 124 to be added by registering the analysis application 124 with the registry service 112 and then associating an appropriate plug-in 126 with the autoanalysis manager 102 thereby providing an efficient means to add functionalities to the analysis system while reducing the need to reconfigure/reprogram the autoanalysis manager 102. While not shown, a similar implementation can be used to incorporate new or additional instruments 120a–120n into the system. In this implementation, the data collection module 114 contains the functionality/definitions of known plug-ins. Hence, the ability to add new instruments 120 and analysis applications 124 to the system 100 or to remove instruments 120 or applications 124 or even to modify instruments 120 and applications 124 may be performed by an update of the registry 112 and potentially the installation of an application plug-in with the autoanalysis manager 102. Hence, the biological analysis system 100 provides for a more flexible/scalable environment than systems of the prior art.

Figure 2:
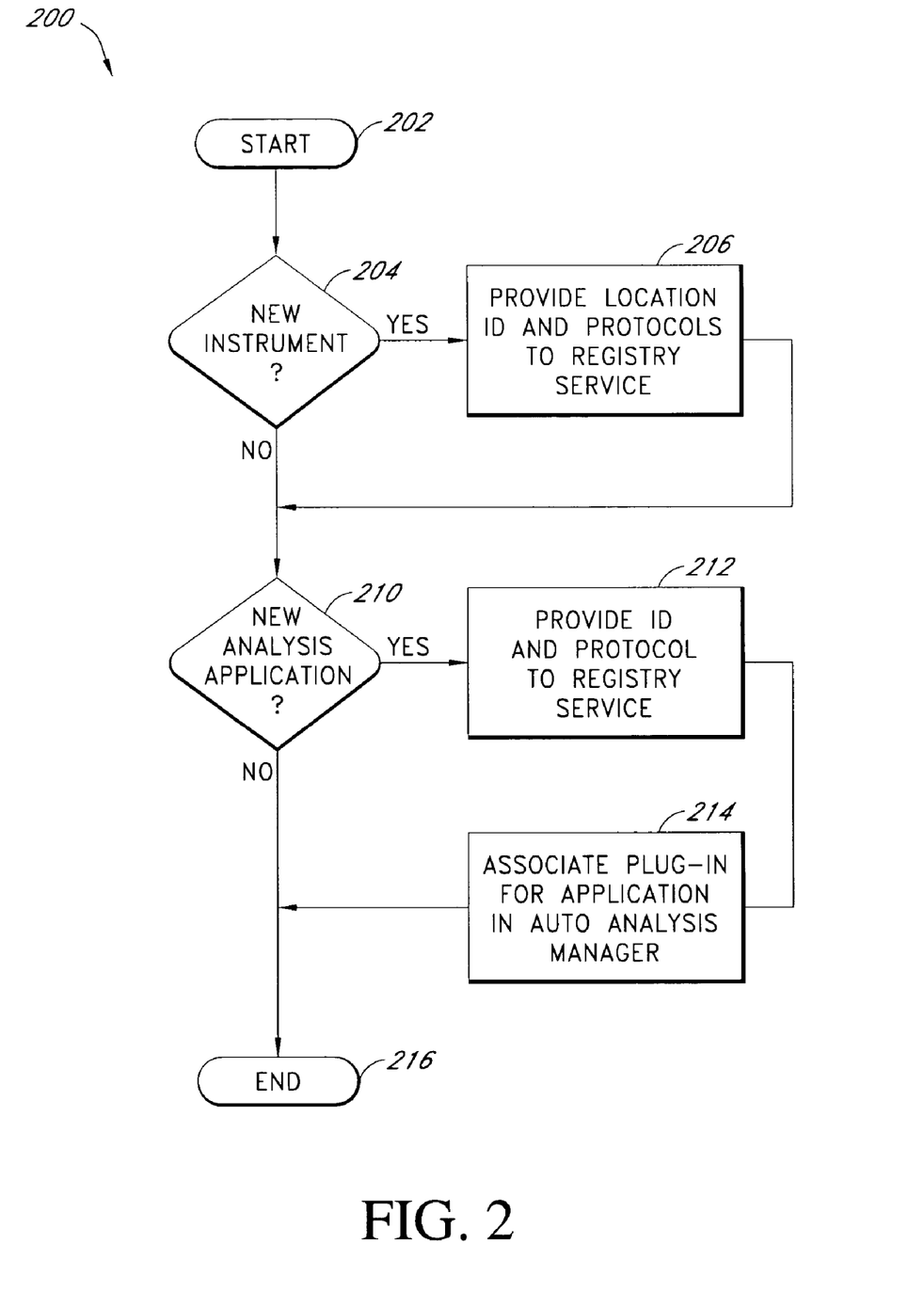
FIG. 2 is an exemplary flow chart illustrating how new instruments and analysis applications can be added into the system of FIG. 1.

Referring now to FIG. 2, a simplified exemplary flow chart illustrates a process 200 that allows for the addition of new instruments or new analysis applications into the biological analysis system 100. Initially, from a start state 202, a determination is made as to whether a new instrument 120 is being added in decision state 204. If a new instrument 120 is being added, information, such as the location, I.D., definitions and protocols for the particular instrument 120 is provided to the registry service 112, in state 206, such that the registry service 206 includes definitions and identifiers for the newly added instrument 120. In one particular implementation, the data collection module 114 associated with a particular instrument 120 is configured such that upon activation of the instrument 120, the module 114 sends a message to the registry 112 indicating its addition to the system 100. The module 114 may also provide the necessary definition to the registry service 112 or if the necessary definitions are already in existence in the registry 112, will provide an indication to the registry service 112 such that the registry service 112 will update the number of instances of this particular instrument 120 within the system 100.

It will be appreciated that the registration of additional instruments into the particular system can also be accomplished through the autoanalysis manager 102 and can even be accomplished manually via a user using, for example, the autoanalysis GUI 106. As such, any of a number of different manners of updating the registry 112 may be utilized to indicate the scope of the present teachings.

Similarly, as indicated in FIG. 2, a determination is also made as to whether a new analysis application is being added in decision state 210. If a new analysis application 124 is being added, then identification information and expected protocols for the new analysis application are provided to the registry service 112 in state 212. As discussed previously, the analysis application 124 can provide this information directly to the registry service 112 itself via the messaging service or, alternatively, this information can be provided to the registry service through the autoanalysis manager 102 or even manually, for example, via the autoanalysis GUI 106.

Once the registry service 112 has been updated as to the protocols and identification information for a selected analysis application, a plug-in 126 that is associated with the newly added analysis application 124 may then be provided to the autoanalysis manager 102 in state 214. Hence, new analysis applications 124 can be added to the system 100 by registering the protocols for the analysis application in the registry service 112 and associating a plug-in with the autoanalysis manager 102 thereby allowing the autoanalysis manager 102 to send signals to the analysis applications 120 and further allowing the autoanalysis manager 102 to have access to the protocol for the analysis application 120 in the registry service 112. Consequently, new instruments and analysis applications 124 can be added to the system without requiring substantial reprogramming of the autoanalysis manager 102 or without requiring substantial modification of the instruments, their associated modules or the associated analysis applications.

In one aspect, the present teachings may be used to integrate instruments and applications into the system in a manner that is substantially transparent to the instrument or application itself. For example, a selected instrument need not be aware of the rest of the components of the system and may be configured to process samples as instructed. The resultant data may then be collected and distributed to the appropriate location within the system via direction by the autoanalysis manager. Likewise data can be provided to a selected application via the autoanalysis manager wherein the application receives the data in an expected format which is processed and the results of which are again collected and distributed to the appropriate location within the system. One desirable result of the aforementioned functionalities is that the autoanalysis manager may be configured to perform scheduling functions and load balancing operations. For example, if more than one instrument or application is used to perform a selected task, the autoanalysis manager may determine which instrument or application is available and assign the task in such a manner so as to distribute workload effectively. This functionality improves the utilization of available resources within the system and helps to avoid potential bottlenecks. Another functionality of the autoanalysis manager is the ability to identify instruments or applications which are offline or busy and redirect tasks accordingly. A further functionality of the autoanalysis manager is the ability to schedule data collection runs or data analysis runs at desired times or intervals. For example, an investigator may define a complete data collection and analysis and schedule the run to be performed during the evening such that the results of the run will be available the following morning. Taken together these features enable improved load-balancing, scheduling, monitoring, and processing of samples and data as compared to systems described in the prior art.

Figure 3:
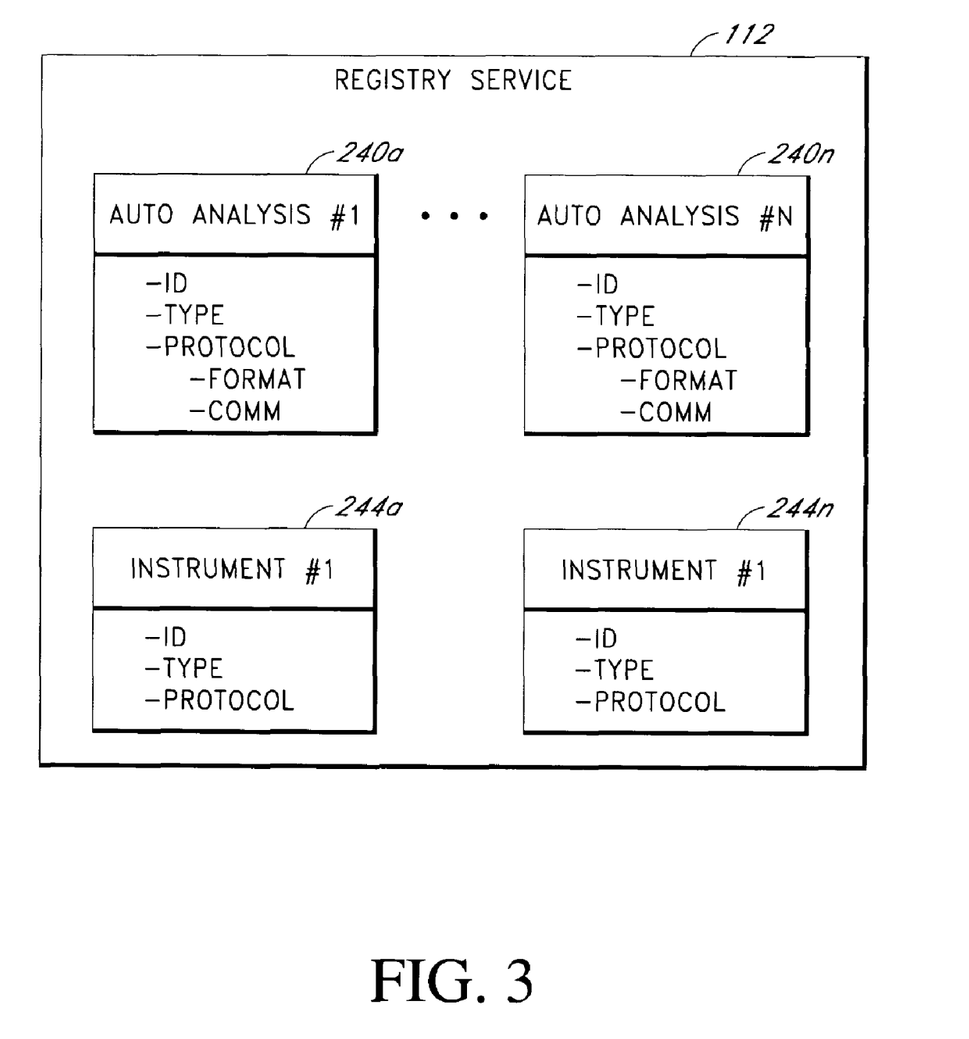
FIG. 3 is a block diagram which illustrates one exemplary organization of a registry service that is a component of the system of FIG. 1.

FIG. 3 is a simplified graphical representation of the information that may be contained within the registry service 112. It will be appreciated that the actual implementation of the registry service 112 can be any of a number of different organizations and as such the organization shown in FIG. 3 should be considered for illustrative purposes only. As indicated in FIG. 3, a plurality of records 240*a*–240*n* may be defined within the registry service 112 for each of the analysis applications 124*a*–124*n*. Each record may include an identifier for the analysis application which provides an indication as to the type of analysis application and the appropriate commands, data formats, and protocols for the analysis application. For example, the protocols define the format in which data from the data collection modules 114 associated with the instruments 120 is to be transmitted to the analysis applications 240. Similarly, there may be a communications protocol 240 which indicates how the analysis application 124 is to be communicated with. In one implementation, the communications protocol provides an identifier (e.g. header) that can be attached to messages broadcast by the messaging service 104 which will result in selected analysis applications to which the identifier is directed accepting and decoding the particular message or communication. Hence, the identifier information may be used by the autoanalysis manager to transfer electronic data captured/generated by the instrument 120 and stored in the data storage location 116 accessible by the analysis application 124.

The autoanalysis manager 102 further provides formatting information to the data collection module 114*a* at or before the time the data is stored in the data storage location 116 such that the data is stored/provided in the format which is appropriate for the analysis application 124 that is to receive the data. Alternatively, the data may be stored in the data storage location 116 in a selected format and later converted to another format which is compatible with the selected analysis application on the basis of the information stored in the registry service. As will be discussed in greater detail below, the autoanalysis manager 102 may utilize a selected communications format for each analysis application 240 when it receives a signal from the data collection module 114 that the data has been captured by the instrument and stored in the data storage location 116 such that the autoanalysis manager 102 may induce the messaging service 104 to broadcast the message which will then be acted on by the analysis application 240. As will also be apparent from the following description, the protocols for the analysis applications may include a wide variety of different requirements for each instrument to capture the data and vary application by application. It will be further appreciated that data from a selected instrument may be captured and saved in a "raw" and "native" format. Subsequently the data may be reformatted in a manner compatible with applications registered with the registry service.

As is also illustrated in FIG. 3, the registry may also contain instrument records 244*a*–244*n* that correspond to each of the instruments 120*a*–120*n*. The instrument records may include identification information for each of the instruments, an indication as to the type of instrument and further, the protocol that defines how the particular instrument is to be used. The protocols can include communications and format protocols in the manner described above in connection with the analysis application records 240. Again, the protocols defining an instrument 120 can include any of a number of different variables or definitions that define the instrument and, of course, may vary instrument by instrument.

Figure 4A:
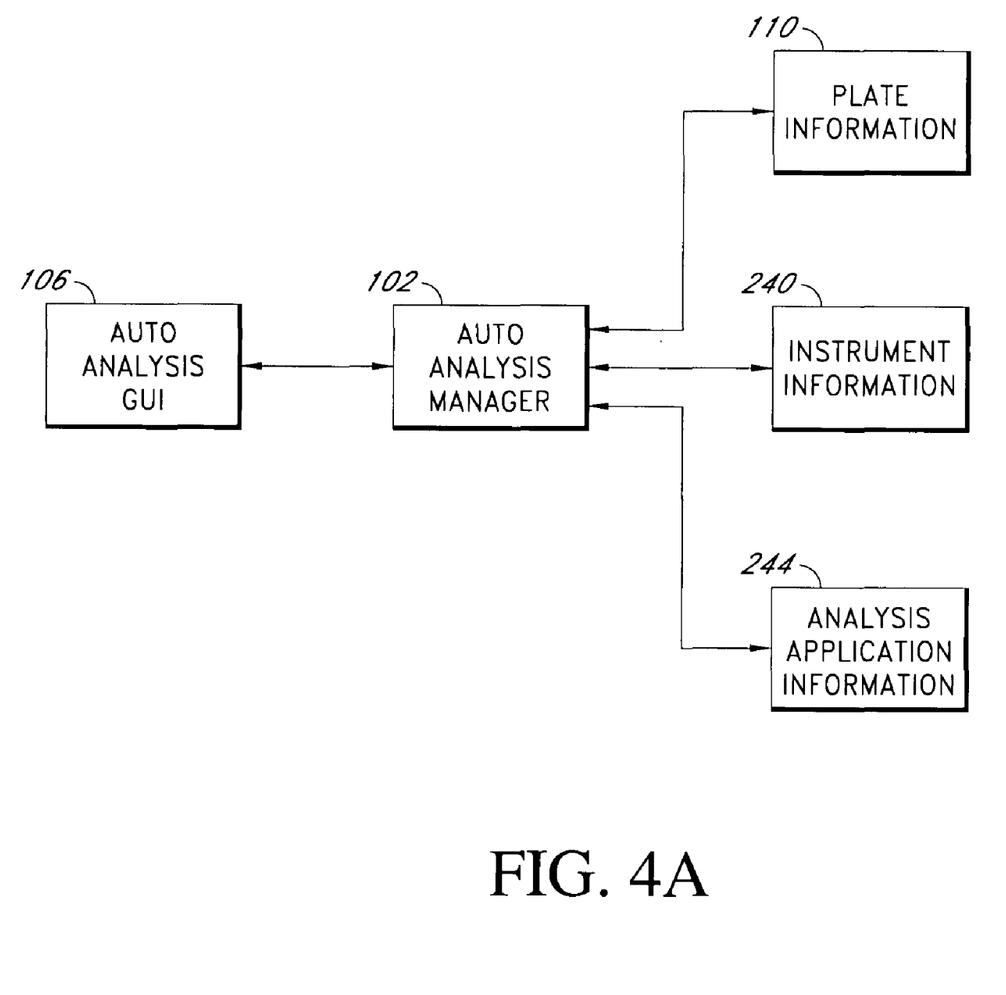
FIG. 4A is a block diagram graphically illustrating the components used by an investigator to program a biological sample evaluation or run.

One advantage in having an integrated system 100 containing an autoanalysis manager 102 or similar daemon interposed between the instruments and the analysis applications, is that this system configuration allows for simplified programming of automated biological sample runs by the investigator. FIG. 4A is a graphical illustration of the resources that may be available to an investigator seeking to develop an automated biological sample run for a selected set of samples. Initially, the investigator can interface with the system 100 via the autoanalysis user interface 106 which, in certain embodiments comprises a graphical user interface. This feature allows the investigator the ability to access certain information provided by the autoanalysis manager 102 such as plate information from the plate database 110. The investigator can also obtain instrument information 244 from the registry service 112 via the autoanalysis manager and can further obtain analysis application information from the registry service 112 via the autoanalysis manager 102.

Hence, the individual who is seeking to perform a process run on one or more samples has, through the GUI 106 and the autoanalysis manager 102, the ability to view available resources within the system 106 and can further view information about a particular plate and the samples positioned therein. Moreover, the individual can program the process run for the samples on particular plates by selecting instruments 120 that will perform particular procedures on the samples and can also have the resultant electronic data provided to selected analysis applications 124 to perform further processing of the electronic information. By having access to the instrument information 244 and the analysis application 240 from the registry service 112, the individual is able to determine which instrument and which analysis applications are appropriate for a particular biological process run. In certain embodiments, the user interface used for developing process runs may be implemented as a scripting language or in other contextual language format. For example, Extensible Markup Language (XML) may be used to facilitate flexibility defining the characteristics, attributes, features, and capabilities of the various components of the system.

Figure 4B:
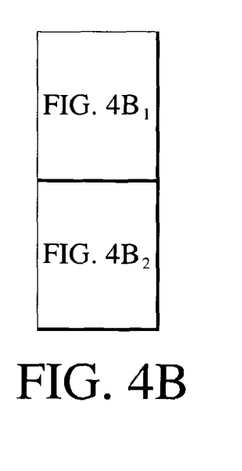
FIG. 4B is an exemplary flow chart illustrating one manner in which the investigator can program the system of FIG. 1 to conduct biological analysis for a plurality of samples.
Figure 4B:
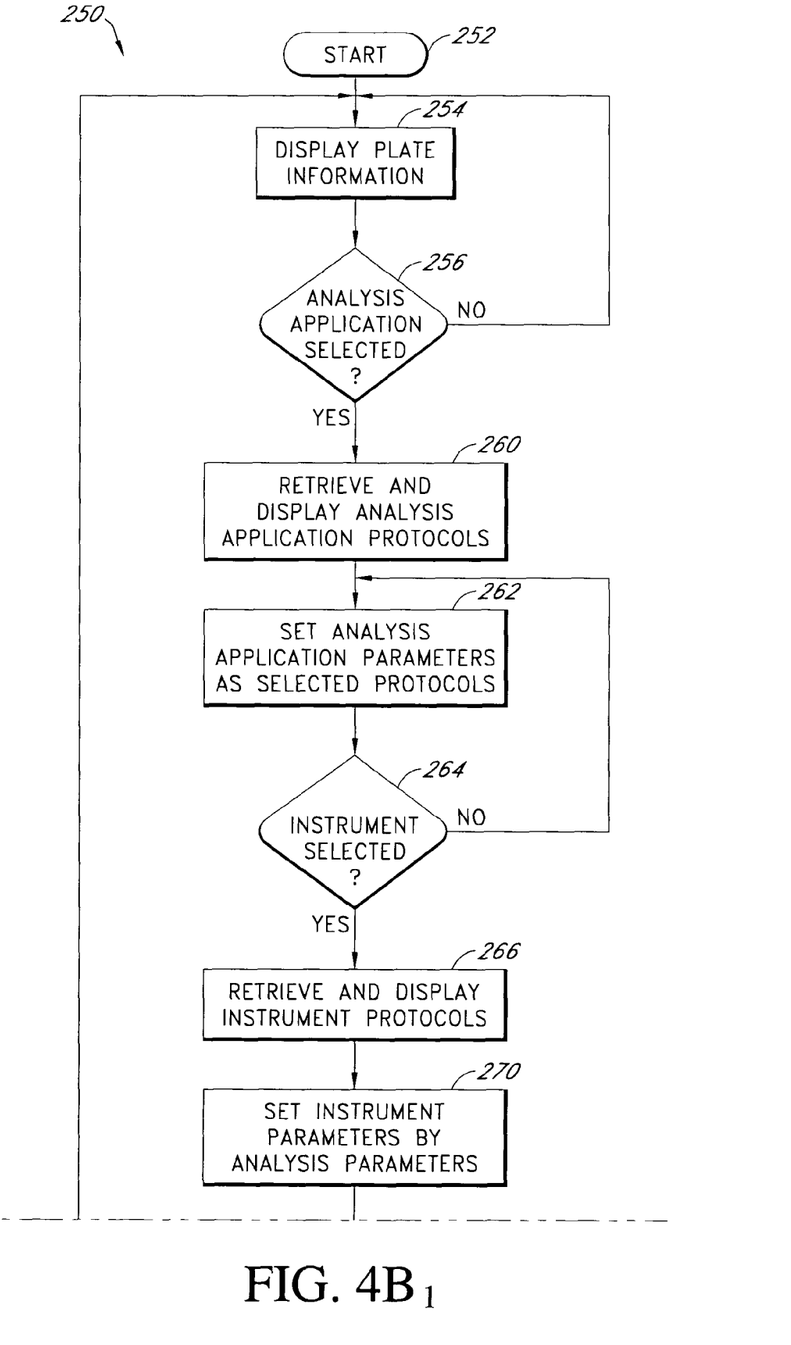
FIG. 4C illustrates exemplary screen shots of the information that can be provided to the investigator programming the system of FIG. 1.
Figure 4B:
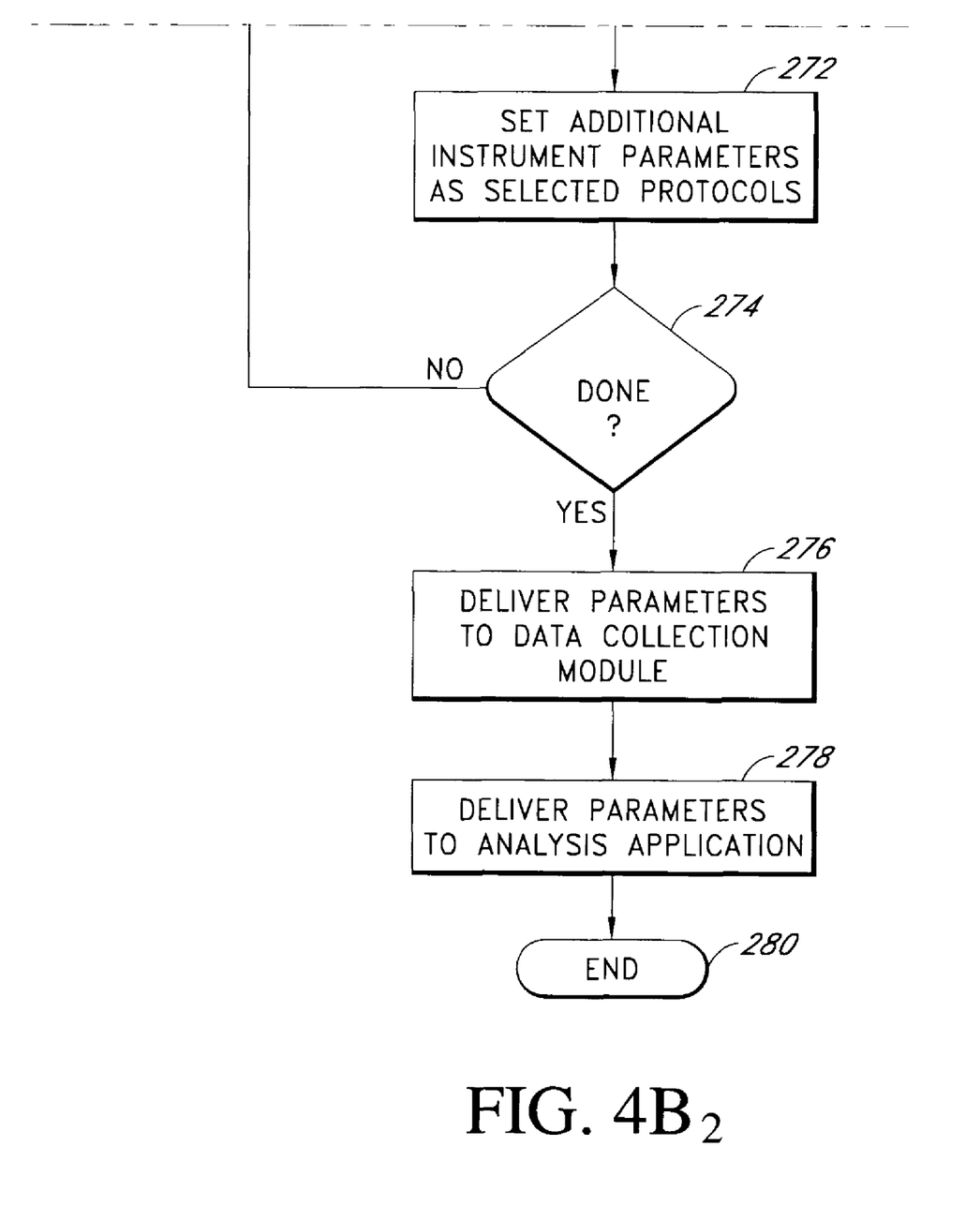

FIG. 4B is an exemplary flow chart illustrating one process by which a biological sample run may be developed and implemented using the system 100. This particular flow chart is exemplary of a particular process flow and will be discussed in connection with FIG. 4C in which the programming of a biological process run can be implemented in a windows-based environment.

Referring to FIG. 4B, the exemplary process flow is as follows, from a start state 252 the plate information is displayed in state 254 to the investigator via the user interface 106. In general, the plate information may previously have been entered into the plate database and the investigator is presented with a graphical representation of the various samples contained within the plate database with associated or relevant identifiers. Once it is determined that the investigator has selected an appropriate analysis application in decision state 256, the application manager then retrieves and displays available protocols for the analysis application(s) in state 260 via the user interface 106. In defining a selected biological process run the investigator may set or configure a variety of parameters in state 262 using the selected protocols that have been retrieved from the registry service 112 and displayed to the user in state 260.

One function of the protocols is to facilitate run design by reducing the number of parameters and variables that must be configured by the user. In various embodiments, the autoanalysis manager recognizes the instructions/samples input by the investigator and populates/configures the appropriate fields/definitions required to perform selected actions desired by the investigator with minimal input or knowledge required from the investigator. Thus the autoanalysis manager may identify an instrument or application within the system appropriate to perform the operations designated by the investigator and configure the process run to provide suitable communications to the appropriate components to perform the process run. One desirable feature of such an implementation is that the investigator is substantially relieved of the burden of having to maintain in-depth knowledge of the location, functional status, or availability of components within the system itself thereby improving the flexibility and ease with which autoanalysis of samples can be conducted.

Once the various analysis application protocols are displayed in state 260, the investigator may configure various conditions for the appropriate protocols available for the selected analysis application and set these as run-time parameters in state 262. If it is determined that the investigator has selected an instrument operation in decision state 264, then the instrument protocols may also be retrieved from the registry service 112 and displayed in state 266. As previously noted some of the instrument protocols may also be modified automatically by the autoanalysis manager 102 in response to the parameters that have been selected for the analysis application in state 270. The autoanalysis manager 102 automatically adjusts appropriate parameters used by the instrument 120 to perform the biological sample run based upon the requirements of the particular analysis application 124. Additionally, the individual may also configure selected or additional parameters, in state 272, for the instruments among the various protocols that have been displayed in state 266.

This particular process of selecting parameters for the analysis application 124 and the instrument 120 generally continues until the investigator has completed the programming of the entire biological sample run at which point the parameters for the instruments are delivered to the associated data collection modules 114 in state 276 and the parameters for the analysis application is delivered to the analysis application in state 278.

Hence, using the graphical user interface 106 and the autoanalysis manager 102, provides a means for the investigator to program a biological sample run that may be implemented by the autoanalysis manager 102. In an automated laboratory, the various sample plates may be delivered to the various instruments selected by the investigator and the various samples on the sample plates may be analyzed in accordance with the selected parameters and the results may then be provided to the selected analysis applications for further processing.

In various embodiments, a previously defined sample run may be re-used and executed at a later time as desired by the investigator. The ability to define re-usable sample runs further improves the flexibility and convenience of using the autoanalysis system. Additionally, rather than having to create process runs from scratch, the investigator may reuse or modify various portions of existing process runs that have been previously defined and saved. This feature improves the speed with which the investigator may complete the configuration or construction of new process runs.

In one particular implementation, the programming of a biological sample run is accomplished using a windows-based environment wherein a sample plate construct 290 is graphically displayed to the individual programming the biological sample run. FIG. 4C is an illustration of one example of the graphic display which may be used in programming a biological process run where the data captured by the instruments is to be analyzed by Applied Biosystems Gene Mapper™ analysis application.

The Gene Mapper™ application includes a variety of parameters that define the process performed on the samples contained in the sample plate. As illustrated, the construct 290 may incorporate a variety of fields defining the instrument operation and a number of these fields may be populated by protocols defined for the Gene Mapper™ application which are registered by the Gene Mapper application in the registry service 112.

As shown in FIG. 4C, there may be an identifier for each of the wells on the sample plate as well as a sample name identifier. Further, comments may also be added to provide additional information about particular samples in particular wells. There may also be a field for sample type which constitutes a parameter that will be provided to the data collection module 114 for a particular instrument 120 which is a protocol defined by the Gene Mapper analysis application and stored in the registry service 112. As shown in this particular example, there are three separate types of sample-type objects, sample, control and ladder, wherein sample a selected sample which is to be evaluated by the instrument 120 and analysis application 124, control defines a known control sample and ladder defines a known reference sample. The ladder and controls are used to identify or aid in the analysis of selected samples and the information provided by these sample-types may be used by the analysis application in conjunction with the selected samples to perform a desired analysis.

As is also illustrated in FIG. 4C, there may exist a field for an analysis group which defines a group that a selected sample belongs to for organizational purposes. As is also illustrated, there may also exist a field for standard dye used by the Gene Mapper analysis application 124 that is registered in the registry service 112. In this particular implementation, Gene Mapper™ analysis application 124 supports red, green, blue, yellow and orange dye colors and this information is provided to the instrument 120 such that the instrument 120 is aware of the dye color associated with a selected well so that when capturing data from the sample, the instrument 120 uses the appropriate data acquisition wavelength for the sample well.

In this particular implementation, there is also a field for panel, which is also defined in the protocol that is registered in the registry service 112. The panel may represent a particular set or series of operations to be performed on a selected sample. Similarly, there is also a field for size standard which defines the type or nature of the standard used by the Gene Mapper analysis application when evaluated the sample data. Again, this information may be stored in a protocol in the registry service 112 for use with a particular application or instrument 120.

As is also indicated, there may be run protocols and analysis protocols which are registered with the registry service 112 and define the manner in which the instrument 120 will process the biological samples such that the resulting data can be accurately processed by the desired analysis application.

From the foregoing, it will be apparent that the system enables the investigator to automatically program both instruments 120 and analysis applications 124 to analyze selected biological samples in a process run by accessing both the instruments 120 and analysis applications 124 protocols in the registry service 112 via the autoanalysis manager 102. Once the particular parameters have been selected for both the instrument operation and the analysis application, the autoanalysis manager can automatically instruct the instruments to process the samples and provide the information to the analysis application which can then further process the data. Subsequently, the data may be stored in a desired location within the system and retrieved/viewed by the investigator.

Figure 5:
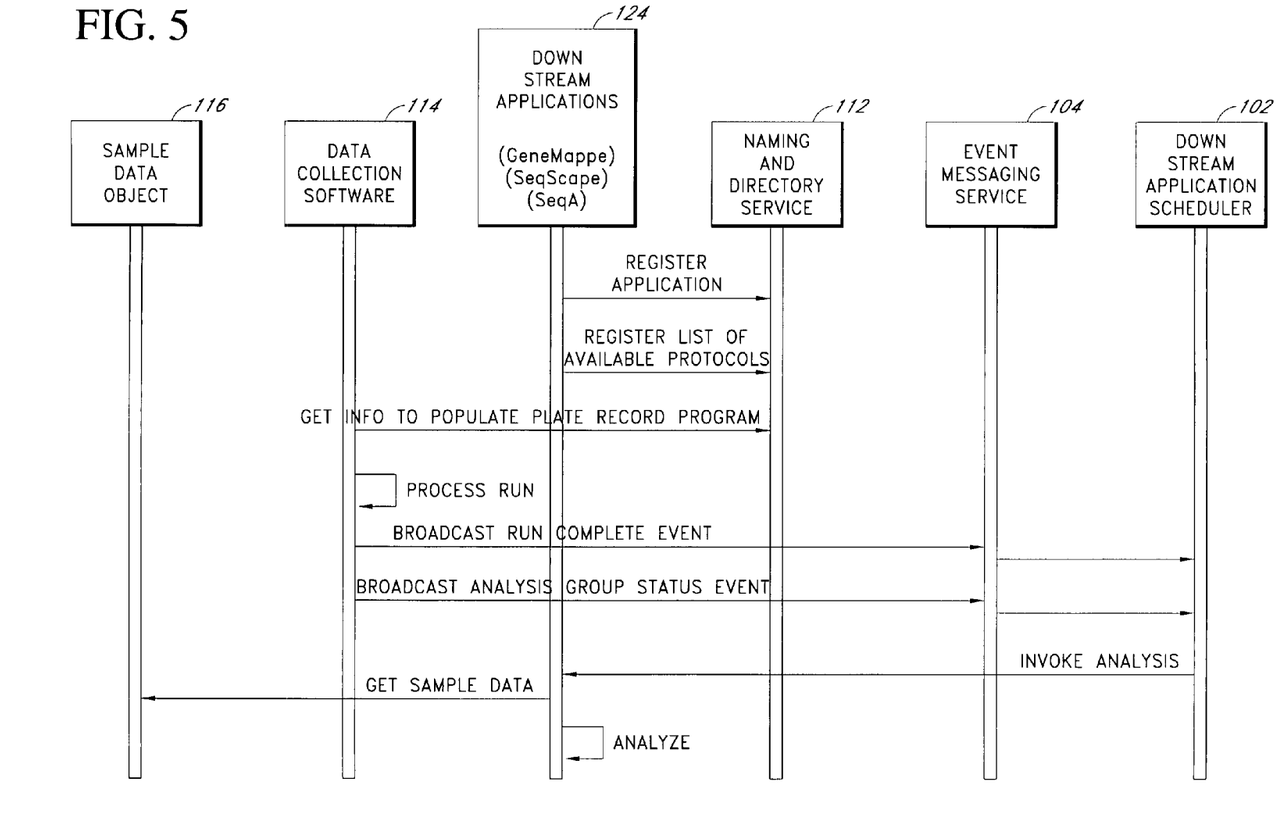
FIG. 5 is a diagram illustrating the operation of the system of FIG. 1 during a biological analysis run.

FIG. 5 is a flow chart that graphically illustrates the operation of the system 100 in performing a biological process run. As is indicated in FIG. 5, when a downstream application, which is generally an analysis application 124, is installed, the application is registered with the registry service 112, referred to in this figure as the naming and directory service. Further, the list of available protocols may also be registered in the naming and directory service 112 upon installation of one of the downstream applications. Various examples of downstream applications are also listed in FIG. 5 and include Applied Biosystems' Gene Mapper applications, Seqscape applications, and SeqA applications. When a biological process run is to be implemented, the data collection software or module 114 fetches from the registry 112 or naming and directory service the information required to populate the plate record in a manner similar to that described above. Subsequently, the data collection module or software 114 instructs the instruments 120 to perform the process run in accordance with the parameters defined in the plate record 290 obtained from the registry 112 or naming and directory service.

Once the process run has been completed and the electronic data has been captured, the data collection software or module 114 then broadcasts a run complete notice or event to the messaging service 104. The format of this message may be a JAVA messaging language (JML) message that is transmitted to the messaging service 104 which then subsequently broadcasts this message to the autoanalysis manager 102 which is referred to in this drawing as the downstream application scheduler. In this particular implementation, the downstream application scheduler is a functionality implemented by the autoanalysis manager 102 which then sends an appropriate signal to the selected downstream analysis application 124 to thereby invoke the subsequent analysis of the electronic data captured by the instruments.

Figure 6A:
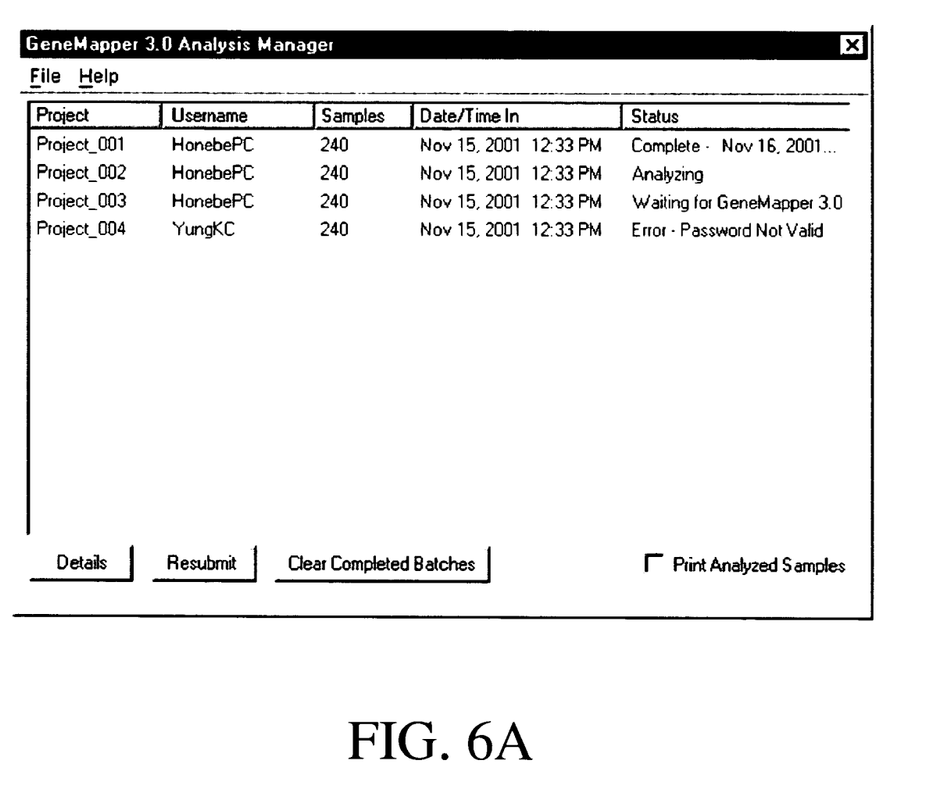
FIG. 6A is an exemplary screen shot illustrating status information that can be provided by the system of FIG. 1 during a biological analysis run.

As is also illustrated in FIG. 5, the data collection software or module 114 may also broadcast status signals or events to the event messaging service 104 which can also be provided to the downstream application scheduler or autoanalysis manager 102. This information can be viewed by an investigator via an interface, such as the user interface 106. FIG. 6A is an example of the status information that the user can see on the user interface 106. The status field provides an indication of the state of completion of a particular project and may be associated with an individual or username who initiated the particular project. Further, it also provides an indication as to the sample number and to the date and time associated with the particular project. As will be appreciated by one of skill in the art the information shown in connection with FIG. 6A is but one an example of the various types of status information that can be provided to an individual monitoring the performance of the system 100 and as such the status information will be expected to vary depending upon the implementation.

Referring again to FIG. 5, once the downstream application scheduler functionality of the autoanalysis manager 102 has received the signal from the data collection software or module 114 that the instruments have collected the desired data from of the physical biological samples, it then issues an appropriate notice or signal to the pre-selected analysis applications 124 for the particular project to initiate their analysis of the data. Consequently, the analysis application 124 then obtains the data that has been stored by the data collection module 114 at a particular data storage location or data object 116, and conducts the subsequent analysis. The location of the data is typically stored in the registry 112 such that when the analysis applications 124 that have been selected to analyze particular data receives the broadcast signal indicating that the data is now available, the applications program accesses the location by looking in the registry 112 for the data location for this particular instrument and then accesses the data accordingly.

From the foregoing, it will be appreciated that the system 100 is easily scalable to include additional analysis applications or instruments. The use of a centralized registry system where the protocols for the instruments and analysis applications can be stored and thereby accessed by the autoanalysis manager allows for automated biological process runs where the instruments are induced to collect and store data in accordance with the requirements of the individual running the project and the data is collected in an appropriate format for subsequent evaluation and analysis by the applications program without requiring reconfiguration or reformatting of the data. As a consequence, the electronic data can be provided directly to the analysis application and the analysis application can then perform its analysis without requiring significant human intervention.

The following examples illustrate various exemplary modes of operation of the autoanalysis system. In various embodiments, the present teachings may be applied to nucleotide or protein analyzers including, for example, the Applied Biosystems 3730 series DNA analyzers and accompanying control and analysis software. A principal benefit realized when applying the methods described herein is that improved throughput may be achieved while reducing data entry and processing complexity; especially in large-scale nucleotide or protein analysis projects. In various embodiments to streamline sample input and extraction, the autoanalysis manager and associated components automatically track and store plate records, run folders, and analysis parameters within a searchable database.

Figure 6B:
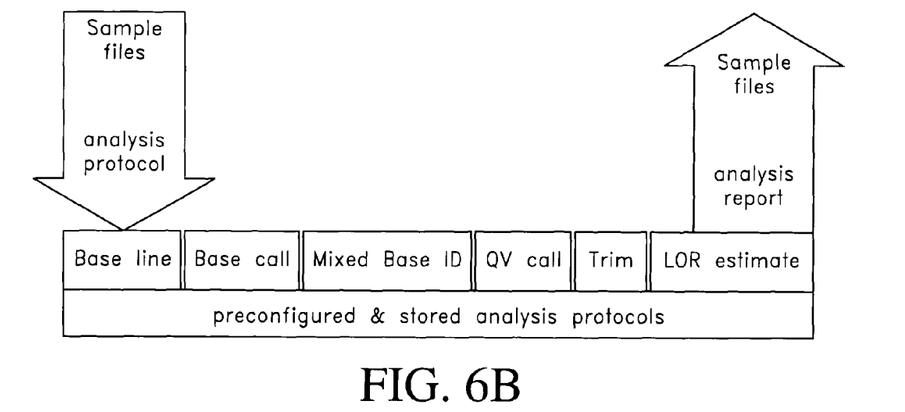
FIGS. 6B–6D illustrate various exemplary data analysis pipelines associated with selected software applications.

FIG. 6B illustrates an exemplary analysis or procedural flow diagram implemented for a sequence analysis application (such a Sequencing Analysis V 5.0 Software developed and distributed by Applied Biosystems, Foster City Calif.). As shown in the illustration, sample data acquired from a selected instrument is initially processed by the autoanalysis manager and sample files generated. These files may then be auto analyzed via one or more analysis software applications.

The analysis software application may reside on the same computer which operates in conjunction with the selected instrument or may be operated on a secondary computer(s) which runs the analysis application independently of the instrument. The autoanalysis manager directs the operation of the analysis application and insures that the appropriate data is made available to the application irrespective of its location with in the system. Furthermore, the autoanalysis manager determines and directs the storage of data after processing by the analysis application (for example by storing or saving in a database).

In one aspect, the application software automatically processes the sample files according to the assigned analysis protocol settings. The analysis pipeline shown in FIG. 6B outlines a process that may proceed when implementing a base-calling method. This pipeline may utilize the functionalities of one or more software applications to perform the various operations within the pipeline wherein the autoanalysis manager is responsible for directing/re-directing the data from one application to the next as necessary. The final output comprises the processed sample files and an analysis report which may contain information including analysis success, quality values, LOR and average signal statistics, and other information relating to the processed samples.

In one aspect, autoanalysis proceeds with sample files generated by a data collection instrument which may be combined with pre-configured analysis protocols. Alternatively, investigators may assign different analysis settings while manually importing sample files into the analysis software. Review of the data generated following data analysis by the software application(s) may be accomplished through a user interface which provides a means to view, edit, analyze, and print from within the analysis application. In one aspect, multiple sample files can be viewed at once within a view window along with relevant data (e.g. quality value (QV) assignments). This functionality provides for easy and rapid viewing, quality assessment and editing of larger amounts of processed data.

Figure 6C:
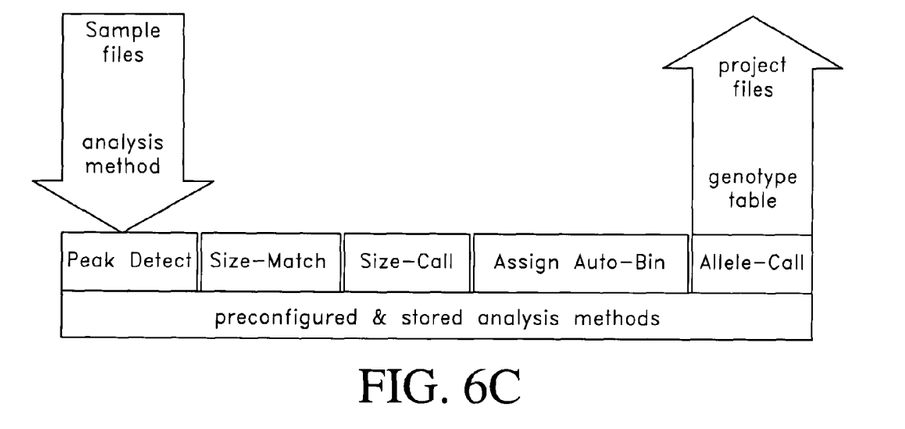
Figure 6D:
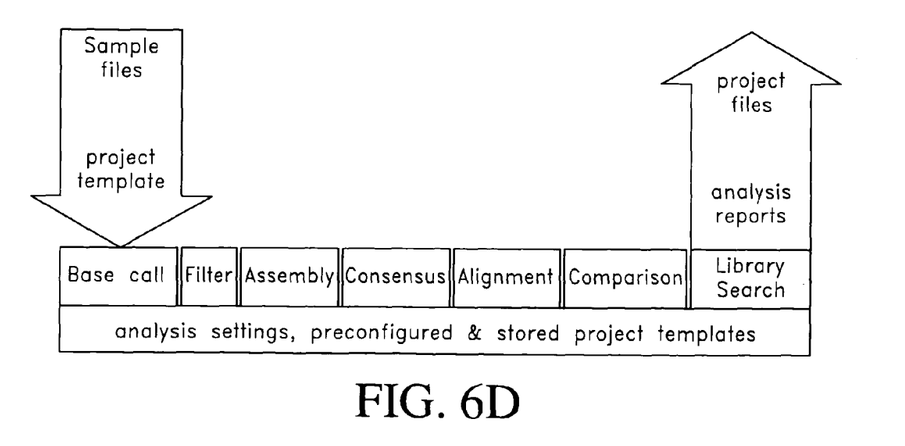

FIGS. 6C & 6D further illustrates exemplary analysis operations of the system in conjunction with analysis applications including GeneMapper v3.0 and SeqScape v2.0 (Applied Biosystems, Foster City, Calif.). In these analysis pipelines (and others), the analysis software may utilize plate records, sample file information, pre-configured analysis methods and size standard calibration data during autoanalysis which may be obtained via the shared autoanalysis manager component. Processed samples can further be viewed, edited, analyzed, and the output printed from within the analysis application.

Although the above-disclosed embodiments of the present invention have shown, described, and pointed out the fundamental novel features of the invention as applied to the above-disclosed embodiments, it should be understood that various omissions, substitutions, and changes in the form of the detail of the devices, systems, and/or methods illustrated may be made by those skilled in the art without departing from the scope of the present invention. Consequently, the scope of the invention should not be limited to the foregoing description, but should be defined by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A system for integrating biological instruments that acquire data from biological samples with analysis applications that analyze the data acquired from the biological samples, the system comprising:

a registry containing protocol information for each of the biological instruments and the analysis applications; and an applications manager that communicates with both the analysis applications and the biological instruments wherein the applications manager has access to the registry and upon receiving instructions to have a biological instrument acquire data from selected biological samples and provide the sample data to selected analysis applications, the applications manager retrieves the protocol information from the registry and directs parameters to be configured for the biological instrument such that the data captured by the biological instrument is made available to the analysis application in a suitable format.

2. The system of claim 1, further comprising a messaging service associated with the applications manager that provides messages to the selected analysis applications when the biological instrument has captured to the data to thereby induce the analysis application to acquire the sample data for subsequent analysis.

3. The system of claim 2, wherein the messaging service is a broadcast message service that broadcasts signals to each of the analysis applications which are recognized and processed by the selected analysis applications to thereby initiate sample analysis using the acquired data.

4. The system of claim 1, wherein the protocols contained within the registry include format protocols for each analysis application defining the format of the data that the analysis application is to receive.

5. The system of claim 4, wherein the protocols further include parameters defining: die colors supported by the analysis application, sample types compatible with the analysis application, size standard files compatible with the analysis application, and analysis protocols for the analysis application.

6. The system of claim 1, further comprising a user interface associated with the applications manager that allows a user to perform functions including:

viewing or defining status of the system, viewing or defining status of individual instruments, viewing or defining status of individual analysis applications, viewing or defining run completion times, viewing or defining instrument operation queues, viewing or defining application operation queues, and viewing or defining users associated with selected process runs.

7. The system of claim 1, further comprising a user interface associated with the applications manager that allows a user to define a sample run comprising a series of operations to be performed in connection with one or more samples; the operations further comprising instrument operations and analysis application operations.

8. The system of claim 1, further comprising a database having stored therein records of the location of samples available for analysis by the system.

9. The system of claim 1, wherein additional analysis applications and instruments can be incorporated into the system by registering an associated protocol within the registry and configuring a suitable plug-in to facilitate communication between the applications manager and the analysis application or instrument to be incorporated into the system.

10. The system of claim 1, wherein each instrument is associated with a plug-in suitable for capturing data generated by the instrument and forwarding the data to other components within the system.

11. The system of claim 10, wherein the plug-in components and the analysis manager comprise software based daemons.

12. A system for integrating a plurality of biological data acquisition instruments that obtain data from samples with a plurality of data analysis applications, the system comprising:

a plurality of instrument components respectively associated with the biological data acquisition instruments;

at least one registry containing instrument protocols for each of the plurality of instrument components and protocols for each of the data analysis applications; and an applications manager that communicates with the plurality of instrument components and the plurality of data analysis applications, wherein the applications manager has access to the at least one registry and includes an associated user interface such that a user can program a series of operations associated with a biological analysis by selecting the samples to be analyzed, selecting the instruments from the registry to process and capture the data from the samples, and selecting the analysis applications from the registry to receive and process the data; wherein additional instruments and additional analysis applications can be added to the system by registering the additional instrument component protocols and the additional analysis application protocols in the registry.

13. The system of claim 12, further comprising a messaging service associated with the applications manager such that the applications manager can provide messages to the analysis application when the instrument has acquired the data to thereby notify the analysis application of the availability of the data for subsequent processing.

14. The system of claim 13, wherein the messaging service is a broadcast message service that broadcasts signals to each of the analysis applications which are recognized and processed by a suitable analysis application to thereby initiate sample analysis using the acquired data.

15. The system of claim 12, wherein the protocols contained within the registry include format protocols for the analysis applications defining the format of the data that each analysis application is to receive.

16. The system of claim 15, wherein the protocols further include parameters defining die colors supported by the analysis applications, sample types compatible with the analysis applications, size standard files compatible with the analysis applications, and analysis protocols for the analysis applications.

17. The system of claim 12, further comprising a database having records of the location of samples available for analysis by the system that the user can access via the user interface and the applications manager can access to configure a biological process run.

18. The system of claim 12, wherein additional analysis applications and instruments can be incorporated into the system by registering an associated protocol within the registry and configuring a suitable plug-in adapted to operate with the analysis applications or instruments to facilitate communication between the applications manager and the analysis applications or instruments.

19. The system of claim 12, wherein each instrument is associated with a plug-in suitable for capturing data generated by a selected instrument and forwarding the data to other components within the system.

20. The system of claim 19, wherein the plug-in components and the analysis manager comprise software based daemons.

21. A system for integrating a plurality of biological data instruments that obtain data from samples with a plurality of discrete data analysis applications, the system comprising:

a plurality of instrument components respectively associated with the biological data instruments;

at least one registry containing instrument protocols for each of the plurality of instrument components and data protocols for each of the data analysis applications wherein the protocols include a messaging protocol;

a data structure containing information describing a plurality of biological samples; and an applications manager that communicates with the plurality of instrument components and the plurality of data analysis applications via a standardized communications protocol, wherein the applications manager has access to the at least one registry and the data structure and includes an associated user interface such that a user can program a series of operations for performing a biological analysis via the user interface such that particular biological samples are processed by selected instruments and upon completion of the processing of samples the data can be made available to the data analysis application for analysis, and wherein the applications manager automatically makes the data available to the data analysis application by sending a standardized communications signal to the data analysis application protocol indicative of the location of the data.

22. The system of claim 21, wherein the applications manager broadcasts messages to each analysis application which are recognized and processed by a selected analysis applications to thereby initiate sample analysis using the acquired data.

23. The system of claim 21, wherein the protocols contained within the registry include format protocols for each analysis application defining the format of the data that the analysis application is to receive.

24. The system of claim 23, wherein the protocols further include parameters defining: die colors supported by the analysis application, sample types compatible with the analysis application, size standard files compatible with the analysis application, and analysis protocols for the analysis application.

25. The system of claim 21, further comprising a user interface associated with the applications manager that allows a user to develop a sample run for one or more selected samples.

26. The system of claim 25, further comprising a plate database having records of each plate of biological samples available for analysis by the system.

27. The system of claim 21, wherein additional analysis applications and instruments can be added to the system by registering an appropriate associated protocol in the registry and an associated plug-in with the applications manager.

28. The system of claim 27, wherein the plug-in comprises a data capture component associated with a particular instrument.

29. The system of claim 28, wherein the plug-in and the analysis manager comprise software-based daemons.

30. A system for integrating a plurality of biological data instruments that obtain electronic data from physical data samples with a plurality of discrete electronic data analysis applications, the system comprising:

a plurality of instrument components respectively associated with the biological data instruments;

at least one registry containing instrument protocols for each of the plurality of instrument components and the protocols for each of the electronic data analysis applications;

a plate data structure containing information indicative of a plurality of biological samples; and an applications manager that communicates with the plurality of instrument components and plurality of discrete electronic data analysis applications, wherein the applications manager has access to the at least one registry and the plate data structure and includes an associated user interface such that a user can program a series of biological analyses by selecting the samples from the plate data structure, selecting the instrument from the registry to capture the electronic data from the physical data samples, and selecting the analysis applications from the registry to receive the electronic data, wherein additional instruments and additional analysis applications can be added to the system by registering the additional instrument component protocols and the additional analysis application protocols within the registry.

31. A system for integrating a plurality of biological data instruments that obtain electronic data from physical data samples with a plurality of discrete electronic data analysis applications, the system comprising:

a plurality of instrument components respectively associated with the biological data instruments;

at least one registry containing instrument protocols for each of the plurality of instrument components and the protocols for each of the electronic data analysis applications wherein each protocol includes a messaging protocol;

a plate data structure containing information indicative of a plurality of biological samples; and an applications manager that communicates with the plurality of instrument components and plurality of discrete electronic data analysis applications via a standardized communications protocol, wherein the applications manager has access to the at least one registry and the plate data structure and includes an associated user interface such that a user can program a series of biological analysis via the user interface such that particular biological samples are processed by particular instruments and upon completion of the processing of particular biological samples the electronic data is made available to the data analysis application for electronic analysis, wherein the applications manager automatically makes the data available to the data analysis application by sending a standard communications signal to the data analysis application protocol indicative of the location of the biological data.

* * * * *